United States Patent
Gonias et al.

[11] Patent Number: 5,902,787
[45] Date of Patent: May 11, 1999

[54] CHEMICALLY MODIFIED A-MACROGLOBULINS, METHODS OF MAKING, AND METHODS OF USING THE SAME IN ANTI-CYTOKINE THERAPY

[75] Inventors: Steven L. Gonias; Donna J. Webb, both of Charlottesville, Va.

[73] Assignee: The University of Virginia Patent Foundation, Charlottesville, Va.

[21] Appl. No.: 08/885,764

[22] Filed: Jun. 30, 1997

[51] Int. Cl.$^6$ .......................... C07K 14/00; A61K 38/02
[52] U.S. Cl. ................. 514/2; 530/402; 530/351
[58] Field of Search ..................... 530/402, 350, 530/351; 435/7.1; 514/2; 524/9, 17, 70; 525/54.1, 54.11

[56] References Cited

PUBLICATIONS

Gonias et al. Inactivation of the Plasma Protease Inhibitor J. Macroglobulin by Antitumor Drug Cis–Dichlorodiamne Platinum (11) J. Biol. Chem. vol. 256, No. 23 pp. 12478–12484 1981.

Hayes et al. Modified $\zeta^2$–Macroglobulins and Their Use as Scavengers for Cytokine and Growth Factors WO 92/07003 Apr. 30, 1992.

MacPherson et al. Antibody Prodcution for Radioligand Assays. Radionucleotides in Clinical Chemistry, First Edition Little, Brown and Company Boston pp. 77–90 1980.

*Primary Examiner*—Lila Feisee
*Assistant Examiner*—Nirmal S. Basi
*Attorney, Agent, or Firm*—Oblon, Spivak, McClelland, Maier & Neustadt, P.C.

[57] ABSTRACT

Chemically modified α-macroglobulin is conformationally locked by cross-linking $\alpha_2M$ with a bi-functional peptide crosslinker, and then modified with methylamine, to provide conformational intermediates with limited conformational change. These modified compounds have a high binding affinity for inflammatory cytokines including TNF-α and IL-1β. When administered in vivo, the modified $\alpha_2M$ (MAC) protects against development of septic shock, and is an effective treatment aid in treating mammals with established septic shock.

7 Claims, 6 Drawing Sheets

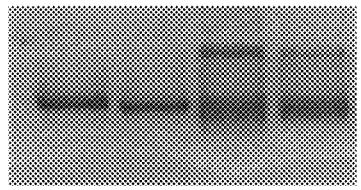
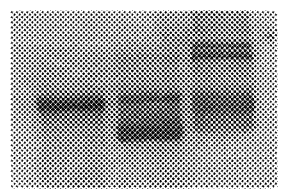
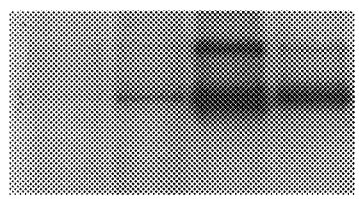
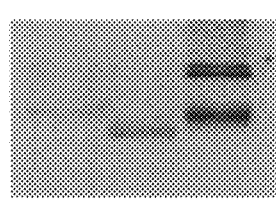
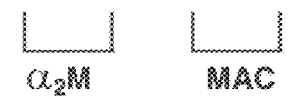
FIG.1A TNF-α
FIG.1B IL-1β
Coomassie-Stained gel
Autoradiograph

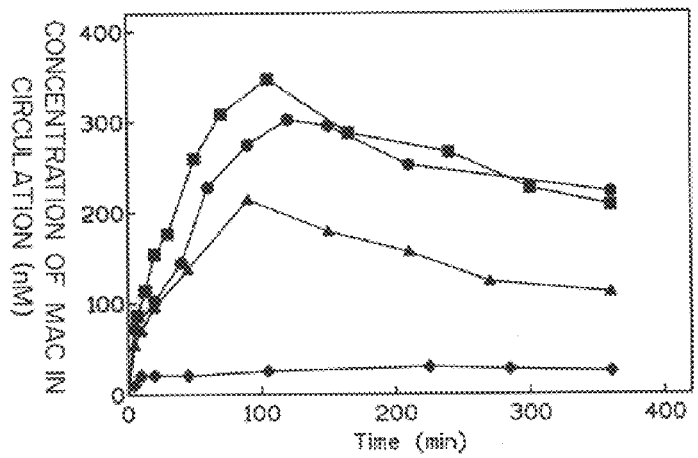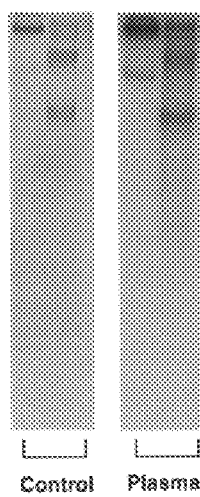

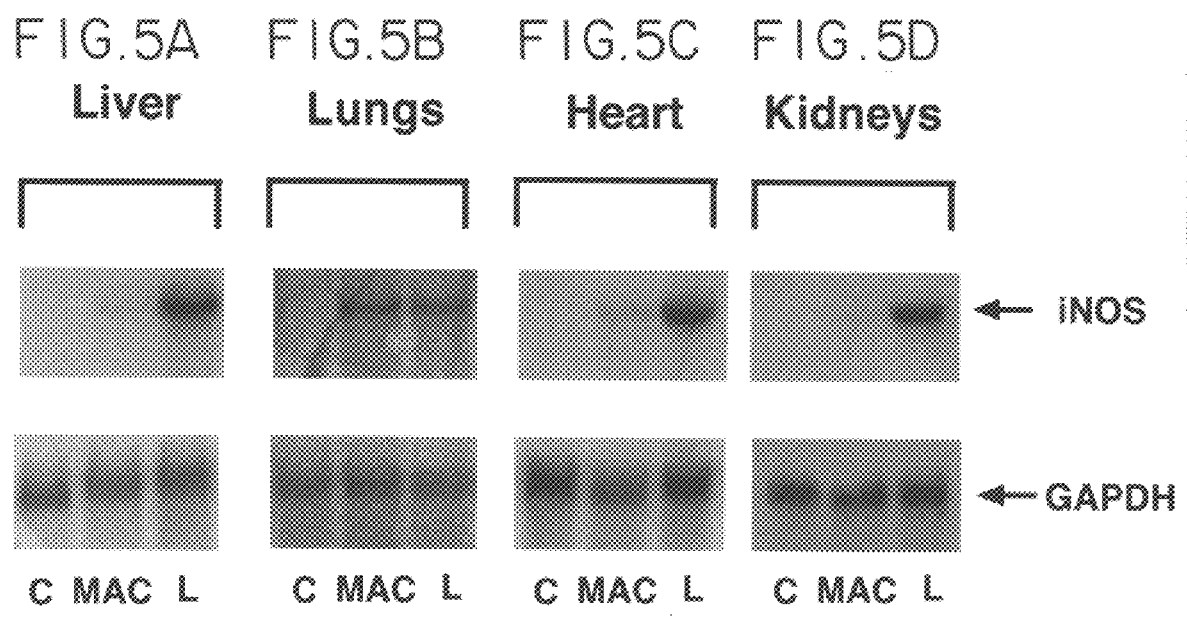

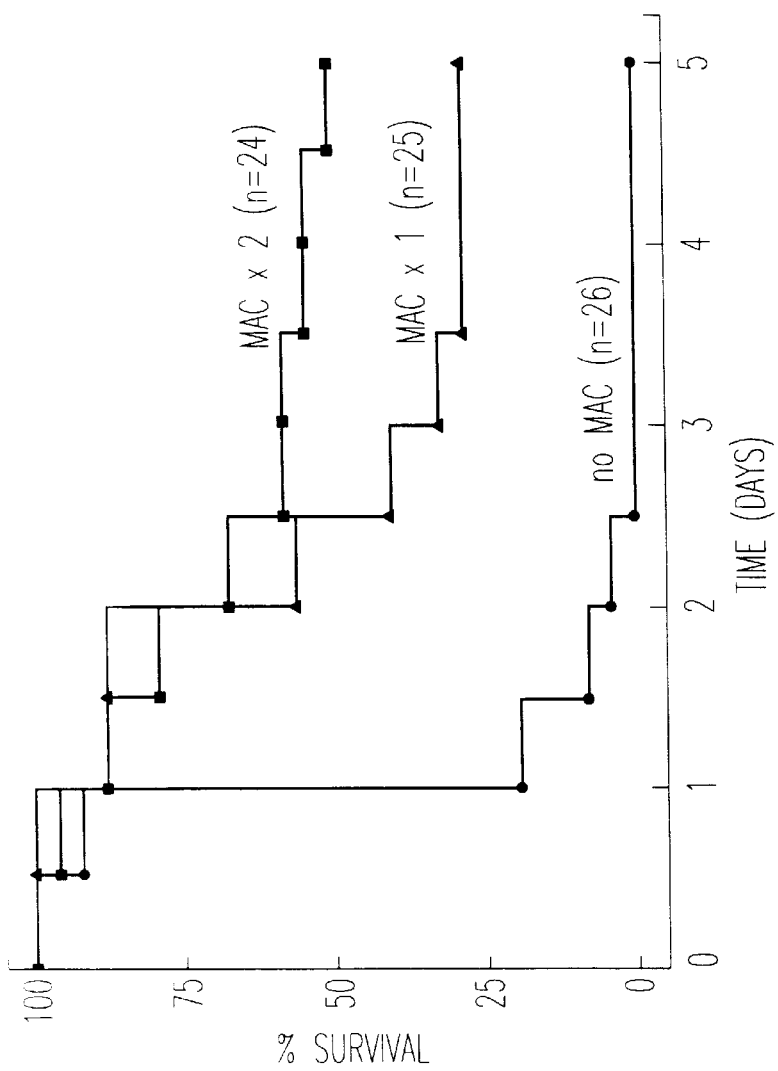
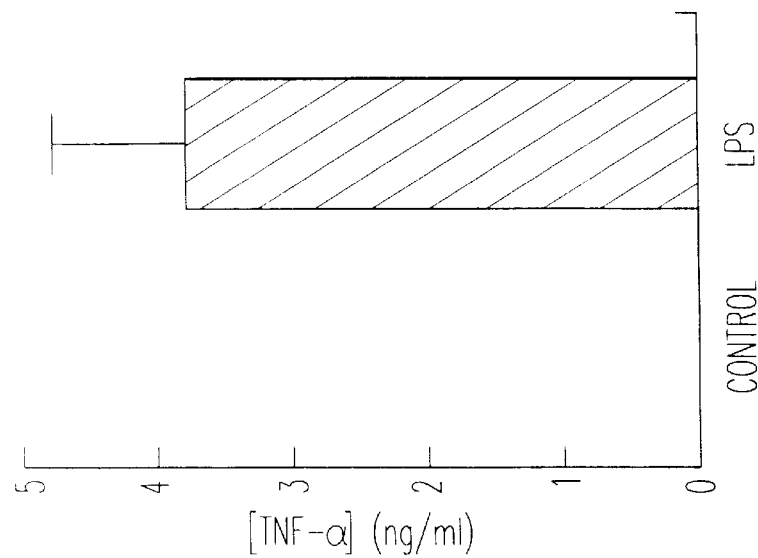

CHEMICALLY MODIFIED A-MACROGLOBULINS, METHODS OF MAKING, AND METHODS OF USING THE SAME IN ANTI-CYTOKINE THERAPY

The United States Government may have rights herein pursuant to NIH/NCI Contract R01 CA53462.

BACKGROUND OF THE INVENTION

FIELD OF THE INVENTION

This invention pertains to a new class of therapeutic agents, modified $\alpha_2$-macroglobulin ($\alpha_2$M) and its utility in binding inflammatory cytokines particularly implicated in septic shock. Specifically, $\alpha_2$M is modified by reaction with a cross-linking agent, to lock the conformational structure of $\alpha_2$M, and then treated with methylamine to give the modified $\alpha_2$M (MAC). MAC is demonstrated to be an effective binder in vitro, and an effective therapeutic, in vivo.

BACKGROUND OF THE INVENTION

Septic shock, a continuing subject of intensive research, remains a leading cause of death in intensive care units, and has proved intractable despite a variety of promising approaches. The body's inflammatory responses frequently complicate bacteremias due to gram negative organisms, or superantigen-producing strains of Staphylococcus aureus and Streptococcus pyogenes. Brandtzaeg et al., Pathology of Septic Shock, 15–37 (Rietschel and Wagner 1996) and Heeg et al., Pathology of Septic Shock, 83–100 (Rietschel and Wagner 1996). Compliment, kinin and coagulation cascades are activated, and a host of defensive cell types, including neutrophils, macrophages and endothelial cells, are stimulated to release inflammatory cytokines. Brandtzaeg and Bone, Ann. Intern. Med. 115:457–469 (1991). These mediators promote the elimination of the infecting organism. The mediators also adversely affect the physiologic functioning of the host, however, and if the process progresses to the point of circulatory compromise and hypotension, the patient slips into a syndrome referred to as septic shock.

There are several bacterial products which elicit symptoms of septic shock. Lipopolysaccharide (LPS) is an amphipathic macromolecule which is derived from the surfaces of gram-negative organisms. Brandtzaeg and Raetz et al., FASEB J. 5:2652–2660 (1991). In experimental animals, LPS initiates the release of inflammatory mediators over a predictable time course. Initially, circulating levels of tumor necrosis factor-$\alpha$ (TNF-$\alpha$) and interleukin-1$\beta$ (IL-1$\beta$) are elevated. Plasma levels of interleukin-6, platelet activating factor, interleukin-8, leukemia inhibitory factor and eicosaniods are also increased. Brandtzaeg, Nakae et al., Res. Commun. Mol. Pathol. Pharmacol. 92:131–139 (1996), Martich et al., J. Exp. Med. 173:1021–1024 (1991) and Waring et al., J. Clin. Invest. 90:2031–2037 (1992). The release of pro-inflammatory cytokines increases expression of inducible nitric oxide synthetese (iNOS), which leads to the production of high levels of nitric oxide, decreased vascular resistance and hypotension. Thiemermann et al., Proc. Natl. Acad. Sci. USA 90:267–271 (1993). Human patients in septic shock release the same inflammatory mediators in a comparable sequence. As a result, LPS-challenge is frequently used to model the inflammatory response to gram-negative bacteremia. Brandtzaeg, supra.

A number of agents that neutralize TNF-$\alpha$ or IL-1$\beta$, including TNF-$\alpha$ neutralizing antibodies, soluble forms of TNF-$\alpha$ cellular receptors and IL-1$\beta$ receptor antagonists have been evaluated as therapeutics in shock. Heumann et al., Pathology of Septic Shock, 299–311 (Rietschel and Wagner 1996), Cohen et al., Amer. J. Med. 99:45S–53S (1995), Butler et al., Science 229:869–871 (1985) and Tracey et al., Nature 330:662–664 (1987). Many of these agents promote survival in animals challenged with LPS, provided that the LPS is administered simultaneously with, or subsequently to, the therapeutic. The same agents prevent shock in animals that are subsequently inoculated with gram-negative bacteria. Existing forms of anti-cytokine therapy demonstrate little or no efficacy, however, when administered to animals after LPS administration, when plasma levels of pro-inflammatory cytokines are already elevated. This corresponds to a condition referred to herein as "established septic shock", i.e., where TNF-$\alpha$ levels are above 1 nanogram/ml. Additionally, existing therapies have been ineffective in treating septic shock in clinical trials. Heumann et al., supra and Cohen et al., supra.

Anti-cytokine therapies are not limited to the treatment of septic shock, however. Inherited and chronic inflammatory disorders, such as rheumatoid arthritis and Crohn's disease are also characterized by cytokine-induced inflammation. No agents are currently effective to directly treat these maladies with cytokine specific intervention.

It has been demonstrated that $\alpha_2$M reversibly binds and regulates the activity of various cytokines. Gonias, Exp. Hematol. 20:302–311 (1992). The highest-affinity interactions of this molecule involve members of the transforming growth factor-$\beta$ (TGF-$\beta$) and neurotorphin families. Crookston et al., J. Biol. Chem. 269:1533–1540 (1994) and Wolf et al., Biochemistry 33:11270–11277 (1994). TNF-$\alpha$ binds to $\alpha_2$M with low affinity ($K_D$ of about 5–10 $\mu$M) while other cytokines, such as interferon-$\gamma$ and ciliary neurotrophic factor, do not bind to $\alpha_2$M at all. Wolf et al, supra. $\alpha_2$M exists in multiple conformations, each with distinct cytokine binding properties. Gonias et al., supra, Webb et al., Biochem. J. 320:351–555 (1996). The conformation of $\alpha_2$M in vivo is modified by proteinases. Conformational characteristics of $\alpha_2$M treated with cis-dichlorodiamineplatinum (II) (cis-Pt) are described in Gonias et al., J. Biol. Chem. 264:9565–9570 (1989). This previously published study examined the conformational characteristics of the resulting partially "locked" compound, but did not characterize its biological or therapeutic activities. The use of cis-Pt to modify $\alpha_2$M was further elaborated on in WO92/07003, which described the binding of TGF-$\beta$1, TGF-$\beta$2 and IL-1$\beta$ by modified $\alpha_2$M molecules, in which the macroglobulin is first reacted with methylamine, by dialysis of $\alpha_2$M against methylamine for 8 hours, and then reacted with cis-Pt, to give a modified $\alpha_2$M. The resulting modified $\alpha_2$M derivative was very different from that addressed here since the $\alpha_2$M was in the fully transformed conformation. Gonias et al., Biochem. Biophys. Acta 678:268–274 (1981). Although the previously described modified derivatives show some ability to bind cytokines, the binding affinity of TNF-$\alpha$ for this protocol, calling for reaction with methylamine, followed by reaction with cis-Pt, was not superior. The $K_D$ for this interaction is approximately 2 $\mu$M, a rather low binding affinity. Ultimately, these molecules have not been demonstrated to be effective therapeutic agents.

Clearance of $\alpha_2$M modified by reaction with cis-Pt is reported in Gonias et al., Biochimica and Biophysica Acta 678:268–274 (1981).

Accordingly, it continues to be a goal of those of skill in the art to develop therapeutics with enhanced binding for both TNF-$\alpha$ and IL-1$\beta$. Further, the desired therapeutic should be effective in treating shock even after plasma levels of these pro-inflammatory cytokines are elevated, particularly after plasma TNF-α has been elevated. Additionally, desirable therapeutics may, in some cases, be safe for administration over a prolonged period of time, when treating chronic inflammatory diseases.

SUMMARY OF THE INVENTION

The above objects, and others made clear in the discussion set forth below, are achieved by the provision of conformational intermediates of $\alpha_2M$, obtained by a reaction of $\alpha_2M$ first with a cross-linking agent which acts as a conformational lock, and subsequently treating the reacted $\alpha_2M$ with methylamine, to obtain the desired conformational change. By pre-treating the molecule with a bifunctional, protein cross-linking reagent, the conformational change induced by reaction with methylamine, which is addressed in WO92/07003, is limited. In contrast, if the order of the treatment is reversed, as described in WO92/07003, and the $\alpha_2M$ is treated with methylamine first, followed by reaction with cis-Pt, the protein undergoes a complete conformational change. The reaction with cis-Pt blocks receptor recognition by direct binding to the receptor recognition site. The structure of the protein is not a conformational intermediate.

$\alpha_2M$ conformationally locked by reaction with cis-Pt, and subsequently reacted with methylamine has demonstrated very high in vitro binding to pro-inflammatory cytokines, and when administered to mice, prevented death in mice that were treated by intravenous injection of LPS at twice the $LD_{50}$. A high binding affinity is considered to be at least 40 fold the ability of the naturally occurring molecule. The modified product (MAC) also inhibited the up-regulation of inducible nitric acid synthase in mRNA in the liver, kidneys and heart of LPS-treated mice. Importantly, even when LPS is injected first, and the MAC subsequently administered, death was prevented in 7 out of 25 and 12 out of 24 mice, depending on the dosage and time separation.

Compounds treated with cis-Pt may not be suitable for chronic administration. It has been discovered that a wide variety of bi-functional, protein cross-linking agents, commercially available, achieve the same "conformational lock", without presenting toxicity problems from prolonged administration. These cross-linking agents, such as 1,5-difluoro-2,4-dinitrobenzene (DFDNB) exhibit enhanced cytokine binding, even superior in some cases to cis-Pt modified products. Thus, cross-linking reagents which react with nucleophilic groups on amino acid side chains, having a close spacing, similar to that present in cis-Pt offer opportunities for prolonged treatment of chronic inflammatory diseases, without exposure to potentially toxic chemicals.

BRIEF DESCRIPTION OF THE DRAWINGS

FIG. 1

Figure 2A:
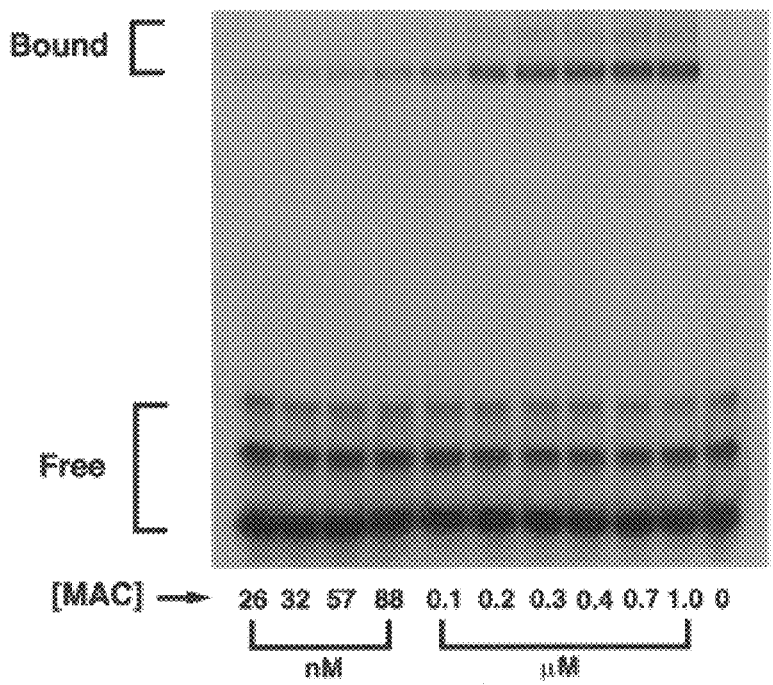

Binding of TNF-α and IL-1β to human and murine $\alpha_2M$. TNF-α was radioiodinated with Iodogen and incubated with native human (h) $\alpha_2M$, native murine (m) $\alpha_2M$, human MAC or murine MAC in PBS containing 2 μM bovine serum albumin (BSA) for 1 h at 37° C. $^{125}$I-IL-1β was purchased from New England Nuclear and incubated with native human $\alpha_2M$ (h-Nat), $\alpha_2M$ treated with methylamine (h-MA), or MAC in the same buffer for 1 h at 37° C. Nondenaturing PAGE was performed on 5% slabs. Gels were stained with Coomassie blue IR-250, dried, and analyzed by autoradiography and PhosphorImager analysis.

FIG. 2

Equilibrium binding of $^{125}$I-TNF-α to human MAC and murine MAC. $^{125}$I-TNF-α was incubated with the indicated concentrations of human MAC or murine MAC in PBS with 75 μM BSA for 30 min at 37° C. The samples were then pulse exposed to BS for 1 min at 22° C. The cross-linking was instantaneously terminated by acidification with 15 mM HCl (final concentration). Samples were denatured in 2.0% SDS for 30 min at 37° C., brought to neutral pH in 100 mM Tris-HCl, and subjected to SDS-PAGE and autoradiography. The autoradiograph of a representative gel (TNF-α reacted with human MAC) is shown in Panel a. Free TNF-α migrated in three bands due to its trimeric structure: monomers, $BS^3$-stabilized dimers, and $BS^3$-stabilized trimers (labeled "free"). Note the increase in radioactivity co-migrating with the MAC bands (bound) as the MAC concentration is increased. In panel b, the amount of cytokine recovered in association with MAC is plotted as a mol-fraction of the total cytokine against the MAC concentration. Results with human MAC (□) and murine MAC (○) are shown (mean±SEM, n=4). Note that the mol fraction saturates near 0.2, reflecting the cross-linking efficiency of the $BS^3$. In panel c, the plotted levels of free and $\alpha_2M$-associated cytokine are the experimentally determined values obtained by analyzing slices of the gel. In this analysis, only a fraction of the MAC-associated $^{125}$I-TNF-α is recovered in the "bound" pool due to the incomplete cross-linking efficiency of $BS^3$. $K_D$ values are determined from the slopes of the graphs in panel c.

FIG. 3

Plasma levels of $^{125}$I-MAC after IP injection. $^{125}$I-MAC (1.0–2.5 mg) was injected IP into CD-1 female mice. At the indicated times, 25 μl of blood were collected from the retroorbital venous plexus of anesthetized mice into heparinized tubes. Radioactivity was determined in a γ-counter. Panel a shows representative experiments in which 1.0 mg (♦), 1.7 mg (▲), 2.0 mg (●), and 2.5 mg (■) of $^{125}$I-MAC were injected. Blood was sampled 1.75 h after IP injection of 2.5 mg $^{125}$I-MAC. Plasma was isolated by centrifugation at 1000×g and subjected to SDS-PAGE (Panel b) and nondenaturing PAGE (Panel c). As a control, the original preparation of MAC was also subjected to SDS and nondenaturing PAGE. The lanes labeled "Control" show the original preparation of purified MAC. The lanes labeled "Plasma" show the plasma samples. In panel b, the "+" indicates the presence of dithiothreitol.

FIG. 4

Survival curves for LPS-challenged mice, with or without MAC pre-treatment. CD-5 female mice were injected EP with 2.5 mg MAC (■) or an equivalent volume of PBS (●). After 60 min, the mice were anesthetized and 57 mg/kg LPS were injected intravenously. The mice were monitored for up to 5 days and then sacrificed. Survival data are presented in panel a. In panel b, mice were injected IP with 2.0 mg MAC (Δ), 1.0 mg MAC (○), or 2.5 mg of native human $\alpha_2M$ (□). LPS was injected 60 min later.

FIG. 5

Northern blot analysis of iNOS mRNA after LPS injection. Mice were injected with 2.5 mg MAC or an equivalent volume of PBS. After 60 min, the mice were anesthetized and injected intravenously with 57 mg/kg LPS or an equivalent volume of LPS. After 10 h, the animals were sacrificed. The liver, lungs, heart, and kidneys were recovered. RNA (20 μg) from each organ was subjected to electrophoresis and Northern blotting. The blots were hybridized with iNOS and GAPDH cDNAs. All blots were subjected to PhosphorImager analysis. The lanes labeled "C" show RNA isolated from mice that were injected IP with PBS and then intravenously with PBS. The lanes labeled "L" shown RNA isolated from mice that were injected IP with PBS and then intravenously with LPS. The lanes labeled "MAC" show RNA from mice treated with IP MAC and then with LPS.

FIG. 6

Survival curves for LPS-challenged mice treated subsequently with one or two doses of MAC. In panel a, CD-1 female mice were anesthetized and injected intravenously with LPS at two-times the $LD_{50}$. After 1 h, the mice were anesthetized and blood was collected from the retroorbital venous plexus and allowed to clot. Serum was isolated by centrifugation at 2000×g and assayed for TNF-α by ELISA (R & D Systems). "Control" represents mice receiving an injection of PBS (n=3), and "LPS" represents mice treated with LPS (n=4). In panel b, mice were anesthetized and injected intravenously with LPS at two-times the $LD_{50}$ (●). One cohort of mice was treated with a single dose of MAC (2.5 mg) 1 h after the LPS (▲). A second cohort was treated with 2.5 mg of MAC, 1 h and 8 h after the LPS (■). The mice were monitored for up to 5 days and then sacrificed.

DETAILED DESCRIPTION OF THE INVENTION

The modified $\alpha_2M$ of the invention is prepared as a conformational intermediate. To secure this family of compounds, and to limit the conformational change resulting from subsequent reaction with a $C_{1-6}$ alkyl-bearing primary amine such as methylamine, purified $\alpha_2M$ is first reacted with a bi-functional cross-linking reagent. Either homo bi-functional or hetero bi-functional agents can be used, which react with various groups found in groups on amino acid side chains. In addition to cis-Pt and DFDNB, a variety of bi-functional crosslinking reagents are commercially available, and can be used. These include, without limitation bis(sulfosuccinimidyl) suberate, bis (diazobenzidine), dimethyl adipimidate, dimethyl pimelimidate, dimethyl suberimidate, disuccinimidyl suberate, glutaraldehyde, m-malemidobenzoyl-N-hydroxysuccinimide, sulfo-M-maleimidobenzoyl-N-hydroxysuccinimide, sulfosuccinidyl 4-(N-maleimidomethyl) cyclohean-1-carboxylate, sulfosuccinimidyl 4-(p-maleimido-phenyl) butyrate and N-succinimidyl 3-(2-pyridyldithio) propionate. Other bi-functional cross-linkers are known to those of skill in the art. The conformationally limited reaction product is then reacted with methylamine. These conformational intermediates bind TNF-α and IL-1β, as well as other cytokines. The binding affinity is orders of magnitude greater than the natural $\alpha_2M$ and $\alpha_2M$ reacted with methylamine. This increased affinity in vitro translates into effective counteraction of the toxicity of LPS in vivo, promoting the survival of LPS-challenged mice, even when administered after the plasma level of TNF-α has elevated following LPS administration.

EXAMPLES

Preparation of $\alpha_2m$ and MAC $\alpha_2M$ was purified from human plasma by the method of Imber et al., J. Biol. Chem. 256:8134–8139 (1981). Murine $\alpha_2M$ was purified from the plasma of CD-1 female mice as previously described. Webb et al., J. Biol. Chem. 271:24982–24988 (1996). To convert $\alpha_2M$ into the fully conformationally transformed state, purified protein was reacted with 200 mM methylamine-HCl in 50 mM Tris-HCl, pH 8.2 for 12 h at 22° C. The preparation was then dialyzed extensively against 20 mM sodium phosphate, 150 mM NaCl, pH 7.4 (PBS) to remove unreacted methylamine. The first step in the preparation of MAC was to react human or murine $\alpha_2M$ with 1.6 mM cis-Pt for 6 h at 37° C. This protocol results in the covalent incorporation of 17 mol platinum per mol $\alpha_2M$. Gonias et al., J. Biol. Chem. 264:9565–9570 (1989). After extensive dialysis, the $\alpha_2M$ was reacted with 200 mM methylamine-HCl. Final preparations of MAC were stored and administered to mice in PBS.

Cytokine Binding Analyses

To compare binding of radioiodinated TNF-α to different forms of $\alpha_2M$, $^{125}$I-TNF-α (1 nM) was incubated with the $\alpha_2M$ preparations (1.0 μM) for 1 h at 37° C. The incubation mixtures were then subjected to nondenaturing PAGE, a method that allows recovery of noncovalent as well as covalent $\alpha_2M$-cytokine complexes. Gonias et al., Ann. New York Acad. Sci. 737:273–290 (1994). $\alpha_2M$ was detected by Coomassie-staining. The TNF-α was detected by autoradiography or Phosphor-Imager analysis.

Nondenaturing PAGE does not allow a quantitative analysis of cytokine binding to $\alpha_2M$ under equilibrium conditions since noncovalent $\alpha_2M$-cytokine complexes may dissociate, to some extent, during electrophoresis. Gonias et al. (1994). To determine equilibrium dissociation constants ($K_D$) for the binding of $^{125}$I-TNF-α to human and murine MAC, we used the $BS^3$-rapid crosslinking method, initially described by Crookston et al. $^{125}$I-TNF-α was incubated with various concentrations of MAC (0.01–1.0 μM) and binding was allowed to reach apparent equilibrium. The solutions were then pulse exposed to $BS^3$ for exactly 1 min. The $BS^3$ crosslinks and thus covalently stabilizes a small but constant percentage of the noncovalent $\alpha_2M$-cytokine complex. All samples were subjected to SDS-PAGE in order to separate covalently stabilized MAC-TNF-α complex from free TNF-α. The TNF-α which was bound to MAC was quantified by slicing the gels and analyzing the slices in a gamma counter. The ratio of free TNF-α (recovered in the gel slices) to MAC-TNF-α complex was plotted against the reciprocal of the MAC concentration (1/MAC). In the resulting linear plot, the $K_D$ is determined from the slope. The method accounts for the partial crosslinking efficiency of the $BS^3$. The presented $K_D$ values assume a single TNF-α binding site per MAC molecule. Crookston et al., Gonias et al. (1994). If there are two noninteracting TNF-α binding sites per MAC, then the $K_D$ for the independent site is two-times the presented value. If the MAC preparation is heterogeneous with regard to TNF-α binding affinity, then the $K_D$ determined by the $BS^3$-rapid crosslinking method is a preparation-averaged value (averaged over all forms of MAC in the preparation).

Pharmacokinetics Analysis of $^{125}$I-MAC $^{125}$I-MAC (1.0–2.5 mg) was injected IP in CD-1 female mice. At various times, blood was collected (25 μl) from the retroorbital venous plexus using heparinized hematocrit tubes. Radioactivity in the blood samples was determined in a γ-counter. Blood, which was recovered 1.75 h after IP injection, was subjected to centrifugation at 1,000×g to isolate plasma. The plasma samples were examined by nondenaturing and SDS-PAGE. $^{125}$I-MAC was detected in the gels by autoradiography.

LPS Challenge Experiments

CD-1 female mice were obtained from Charles River Breeding Laboratories. Animals were kept on a 12:12 h dark-light cycle. Mice were anesthetized with diethyl ether prior to intravenous injections of LPS. All animals were observed on a continuous basis. Those entering a moribund condition were euthanized by cervical dislocation under anesthesia. All protocols executed here were subjected to review and judged consistent with the Public Health Service (USA) Policy on Humane Care and Use of Animals.

Northern Blot Analysis

MAC (2.5 mg) or an equivalent volume of PBS was injected EP in CD-1 female mice. After 60 min, LPS (57 mg/kg) or PBS was injected intravenously under anesthesia. All animals were sacrificed after 10 h. The liver, heart, lungs, and kidneys were recovered. These organs were homogenized separately in Trizol and total cellular RNA was isolated in Trizol according to instructions from the manufacturer (Life Technologies, Inc.). Equal amounts of RNA (20 μg) from each organ were subjected to electrophoresis in 1.0% (w/v) agarose and electroblotted to Zeta probe nylon membranes (BioRad). The iNOS cDNA in pUC19 was generously provided by Drs. Qiao-wen Zie and Carl Nathan, Cornell University Medical College, New York, N.Y. A 645-nucleotide fragment was excised with HindII and BamHI for use as a Northern blot probe. The fragment was labeled with $[\alpha\text{-}^{32}P]dCTP$ by random oligonucleotide-primed synthesis and incubated with the membrane at 42° C. in 5×SSPE, 5×Denhardt's solution 50% formamide, 0.1% SDS, and 100 μg/ml salmon sperm DNA for 24 h. Membranes were washed two times with 5×SSPE, 0.5% SDS at room temperature for 10 min. and then two times with 1.0×SSPE, 1.0% SDS at 65° C. for 10 min. The membranes were then exposed to Kodak X-Ormat film or analyzed in a PhosphorImager. As a control for RNA load, the blots were also hybridized with a $[\alpha\text{-}^{32}P]dCTP$ cDNA for glyceraldehyde-3-phosphate-dehydrogenase (GAPDH).

Pro-Inflammatory Cytokines Bind to MAC

The cis-Pt/methylamine reaction-protocol was executed with purified human and murine $\alpha_2M$. The two MAC preparations were thoroughly dialyzed so that free cis-Pt and methylamine were not present. $^{125}$I-TNF-α (1 nM) was then incubated with human $\alpha_2M$ (native form), human MAC, murine $\alpha_2M$ (native form), and murine MAC (each at 1.0 μM) for 1 h at 37° C. The samples were subjected to nondenaturing PAGE, a method that allows demonstration of noncovalent as well as covalent complexes. Free $^{125}$I-TNF-α did not migrate near the $\alpha_2M$ bands (results not shown). Thus, recovery of radioactivity in association with the Coomassie-stained $\alpha_2M$ reflected TNF-α that was bound to the $\alpha_2M$. As shown in FIG. 1, binding of TNF-α to native human $\alpha_2M$ was not detected, confirming previous results. Crookston et al, Wollenberg et at., Amer. J. Pathol. 138:265–272 (1991). TNF-α bound to native murine $\alpha_2M$; however, the level of binding was low. The MAC preparations bound greatly increased amounts of $^{125}$I-TNF-α. The low-mobility bands, observed by Coomassie-staining, are probably due to intermolecular cross-linking of the $\alpha_2M$ since the concentration of cis-Pt used to modify the $\alpha_2M$ was high. Gorias et al., J. Biol. Chem. 256:12478–12489. cis-Pt-dimerized MAC retained TNF-α binding activity.

Borth and Luger, J. Biol. Chem. 264:5818–5825 (1989), first demonstrated that IL-1β binds primarily to $\alpha_2M$ that has undergone conformation change and not to native $\alpha_2M$. FIG. 1 compares the binding of $^{125}$I-IL-1β to native human $\alpha_2M$, methylamine-modified human $\alpha_2M$, and human MAC. Methylamine-modified $\alpha_2M$ bound IL-1β preferentially, compared with native $\alpha_2M$, confirming the work of Borth and Luger. MAC bound greatly increased amounts of IL-1β compared with either of the two previously characterized forms of $\alpha_2M$. Thus, MAC has the potential to neutralize at least two of the major pro-inflammatory cytokines of endotoxic shock.

Although nondenaturing PAGE is effective for comparing cytokine-binding to various $\alpha_2M$ derivatives, this technique cannot be used to determine equilibrium binding affinities since noncovalent $\alpha_2M$-cytokine complexes partially dissociate during electrophoresis. Gonias et al. (1994). Thus, we used a previously described $\alpha_2M$/cytokine complex-stabilization method, developed in our laboratory, to determine equilibrium dissociation constants for the binding of $^{125}$I-TNF-α to MAC in solution. Crookston et al., Gonias et al. 91994). We considered it important to determine constants with both human MAC and murine MAC so that we could select the optimal preparation for animal model testing. The advantage of studying murine MAC is the allogeneic system; however, human MAC would be the preferred reagent for eventual translation into clinical trials.

Figure 2B:
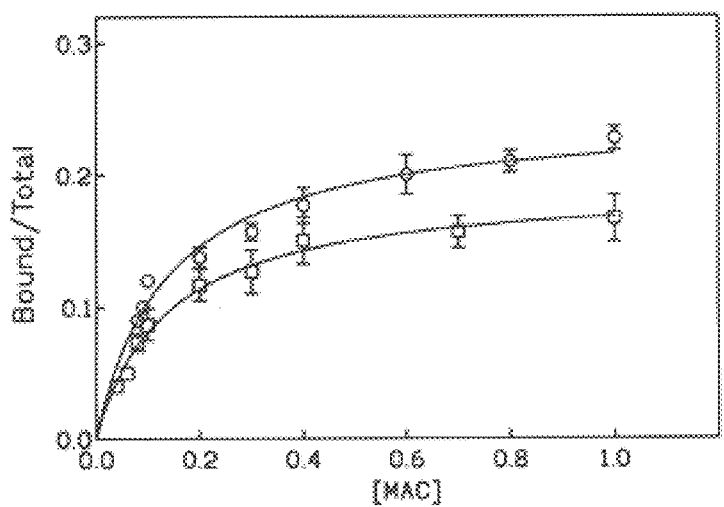
Figure 2C:
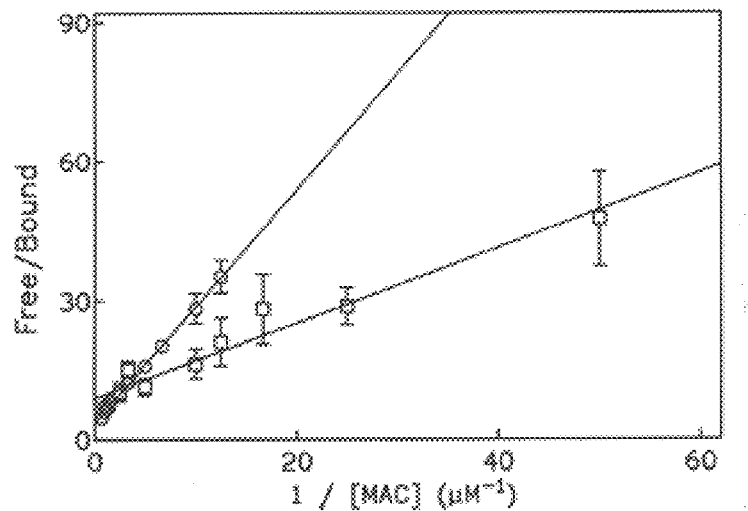

To determine $K_D$ values, radioiodinated TNF-α was incubated with increasing concentrations of MAC and binding was allowed to reach apparent equilibrium. The solutions were then pulse-exposed to the rapid-crosslinking reagent, bis(sulfosuccinimidyl)suberate($BS^3$). The $BS^3$ stabilizes a small but constant fraction of the $\alpha_2M$-cytokine complex which can then be detected by SDS-PAGE (FIG. 2, panel a). $^{125}$I-TNF-α binding was plotted as a function of $\alpha_2M$ concentration (panels b and c). The $K_D$ for the binding of TNF-α to murine MAC was 590±60 nM. The $K_D$ for the binding of TNF-α to human MAC was substantially lower (80±20 nM). The method for calculating the $K_D$ accounts for the $BS^3$-crosslinking efficiency, the time of $BS^3$-pulse exposure, and any complex that may be covalent in the absence of crosslinker. Since the MAC preparations are probably heterogeneous, the binding constants represent mean $K_D$ values, determined by averaging over the entire population of $\alpha_2M$ molecules in the MAC preparation.

Human MAC and murine MAC bound TNF-α with considerably greater affinity than native, unmodified human $\alpha_2M$, Crookston et al.; however, the equilibrium binding analysis suggested that human MAC has the greatest potential for neutralizing TNF-α in vivo. Thus, we initiated our animal-model testing with human MAC.

Pharmacology of MAC in Mice

In initial experiments to determine whether human MAC is toxic in mice, 1.0, 2.5, or 5.0 mg were injected intraperitoneal (IP). Equivalent concentrations of human $\alpha_2M$ (native, unmodified form) were injected IP in separate animals, as a control. Each concentration of MAC or human $\alpha_2M$ was studied in duplicate. All of the mice tolerated IP $\alpha_2M$ or MAC without outward changes in physiology (neurologic status, respiratory rate, eating and drinking, general behavior). The animals were sacrificed after 5 days of observation.

Studies analyzing the transfer of MAC from the intraperitoneal space into the circulation are presented in FIG. 3. In these experiments, 1.0–2.5 mg of $^{125}$I-MAC were injected IP and levels of radioactivity were determined in plasma samples. Panel a shows the concentration of MAC in the plasma as a function of time, assuming that all of the radioactivity represents intact protein. When 2.5 mg of MC were injected, plasma concentrations maximized at over 300 nM. The MAC concentration was sustained at over 200 nM for greater than 5 h. When 1.0 mg of MAC was injected, the plasma concentration peaked at 30 nM. Thus, maximum plasma concentrations of MAC were not linearly correlated with the amount of MAC injected IP. SDS-PAGE experiments demonstrated that the $^{125}$I-MAC recovered from the plasma had not ben proteolyzed (panel b). Nondenaturing PAGE experiments suggested that the conformation of the recovered $^{125}$I-MAC was also unaltered compared with the original preparation (panel c). Thus, the assumption that plasma radioactivity represents intact protein was valid.

MAC Protects Mice from LPS-Toxicity

Figure 4A:
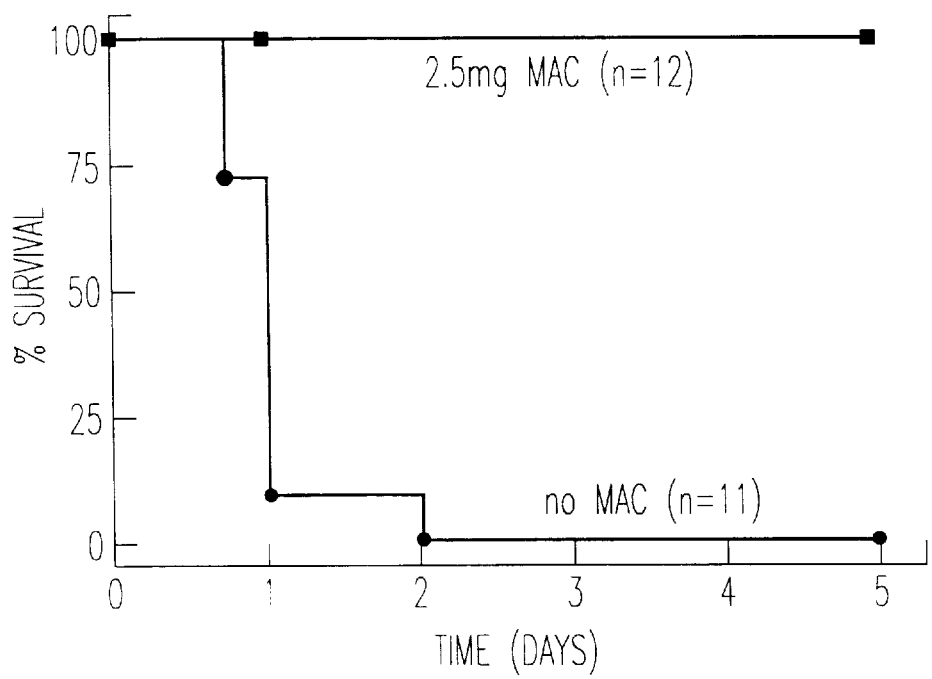
Figure 4B:
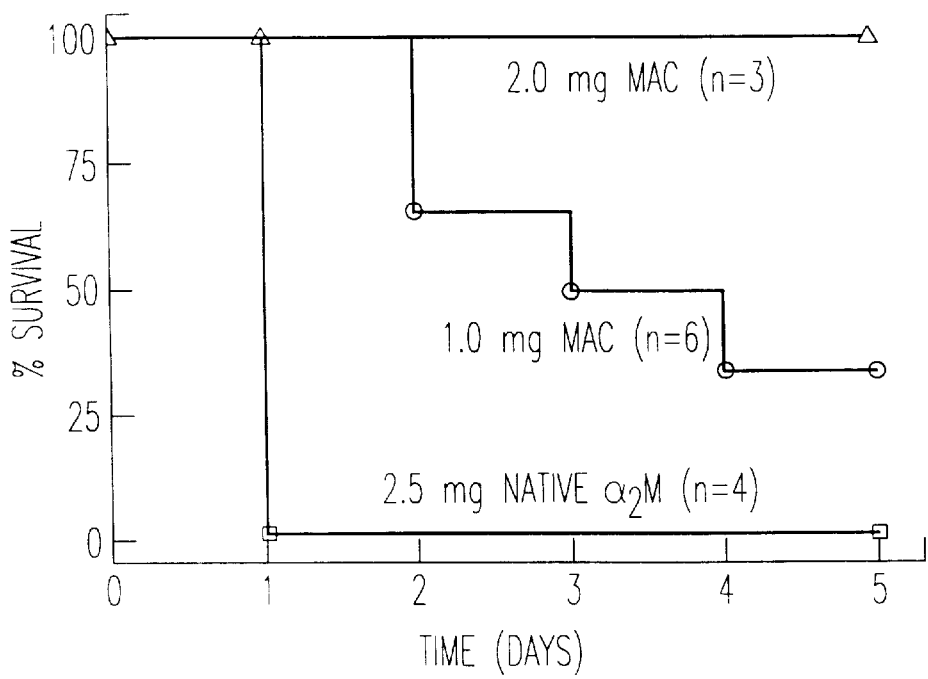

In the next series of experiments, the ability of MAC to counteract the activity of LPS was studied. The concentration of LPS injected intravenously (57 mg/kg) was two-times the $LD_{50}$ reported by the supplier (Difco Laboratories). As shown in FIG. 4 (panel a), the LPS was rapidly lethal; 25/26 mice survived less than 48 h after injection. By contrast, 12/12 mice that were pre-treated with 2.5 mg MAC, by IP injection 60 min prior to the LPS, survived and were without signs when sacrificed at 5 days. The reason for preinjecting the MAC was to allow optimal absorption into the plasma.

The activity of MAC in the LPS challenge experiments was dose-dependent (FIG. 4, panel b). MAC, at 2.0 mg per mouse, was uniformly efficacious. By contrast, MAC at 1.0 mg per mouse, was only partially efficacious. Even though half of the mice treated with 1.0 mg of MAC died within 5 days, all of the mice survived longer (2–5 days) than did animals that were not treated with MAC. As a control, 2.5 mg of native human $\alpha_2$M was injected IP, 60 min prior to intravenous injection of LPS; 4/4 animals died within 24 h, demonstrating that only the modified form of $\alpha_2$M is active as an inhibitor of LPS toxicity.

MAC Significantly Decreases LPS-Induced iNOS mRNA in Mice

Nitric oxide is generated late in the course of LPS-challenge and may serve as the major mediator of circulatory collapse. Thiemermann et al. Inhibitors of iNCS reverse the hypotension caused by LPS or TNF-$\alpha$ in experimental animals. Kilbourn et al., Proc. Natl. Acad. Sci. USA 87:3629–3632 (1990) and Parella et al., Proc. Natl. Acad. Sci. USA 93:2054–2059 (1996). Thus, we performed experiments to determine whether MAC prevents the increase in iNOS expression caused by LPS. iNOS mRNA was undetectable in the liver, lungs, heart, and kidneys of mice that were not treated with LPS (FIG. 5). Substantial levels of iNOS mRNA were detected in all four organs 10 h after intravenous injection of LPS. Pretreatment of the mice with MAC decreased LPS-induced iNOS mRNA by 89±4% (n=4) in the kidneys, 87±9% (n=3) in the liver, and 79% (n=2) in the heart. MAC did not significantly affect iNOS mRNA in the lungs. This result was interesting since it was previously shown that LPS-induced iNOS in the lungs is less effectively suppressed by TGF-$\beta$1 compared with iNOS in other organs. Parella et al. Similarly, Cunha et al., Immunol. 81:1162–1172 reported that TNF-$\alpha$ and IL-1$\beta$-specific antibodies suppress iNOS in the lungs less effectively than iNOS in other organs. These previous results and ours suggest that iNOS expression in the lungs may be directly induced by LPS or by an LPS-induced lung cytokine which is resistant to MAC and the specified neutralizing antibodies.

MAC Reverses LPS-Induced Toxicity in Mice

To determine the time required to initiate the cascade of inflammatory mediators after injection of LPS, plasma levels of TNF-$\alpha$ were measured. FIG. 6, panel a, shows that the plasma concentration of TNF-$\alpha$ was substantially elevated (3.8±0.9 ng/ml, n=4) 1 h after IV injection of our standard LPS dose (two-times the $LD_{50}$). TNF-$\alpha$ was undetectable in the plasma of mice that received vehicle instead of LPS.

In the next series of experiments, mice were challenged with LPS, at two times the $LD_{50}$, and then treated with a single dose of MAC (2.5 mg) 1 h later or, with two doses of MAC, 1 and 8 h after administration of the LPS. When the first dose of MAC was administered, the plasma TNF-$\alpha$ concentration was already substantially elevated. Furthermore, since the MAC was injected IP, maximum plasma levels were not achieved until 3 h after LPS challenge. As shown in FIG. 6b, 7/25 mice (28%) that were treated with one dose of MAC survived and were without signs of shock when sacrificed at 5 days. In the cohort treated with two doses of MAC, 12/24 mice (50%) survived the entire 5 day protocol. At the time these animals were sacrificed, they were eating and drinking normally, and without signs of cardiovascular or neurologic compromise. Both MAC treatment protocols significantly improved survival compared with the control (p<0.001) as determined by log-rank test and by the Wilcoxon rank sum test (statistical analyses performed using the SAS statistical package).

Administration of MAC may be IP or IV, although IV infusion is clearly preferred. Dosage values will vary with the individual, the severity of the condition and similar factors. In general, a dose will be between 50 mg and 1.5 g of MAC, preferably 250–600 mg, in a carrier acceptable for IV administration. A dose may be repeated, if the condition persists.

What is claimed is:

1. A method of binding TNF-$\alpha$, IL-1$\beta$ and combinations thereof comprising combining a compound prepared from $\alpha_2$ macroglobulin ($\alpha_2$M) wherein said $\alpha_2$M has been cross-linked by reaction with a bi-functional peptide cross-linking agent to limit the ability of said $\alpha_2$M to undergo conformational changes, and subsequently reacting said limited $\alpha_2$M with a $C_{1-6}$ alkyl-bearing primary amine, with a system comprising TNF-$\alpha$, IL-1$\beta$ or mixtures thereof.

2. The method of claim 1, wherein said system is in vitro.

3. The method of claim 1, wherein said system comprises a mammal.

4. The method of claim 3, wherein said mammal is a human.

5. A method of protecting a, mammal against septic shock, comprising administering to said mammal, in advance of elevated TNF-$\alpha$ plasma levels, an amount of a compound prepared by reacting $\alpha_2$M with a bi-functional peptide cross-linking agent to limit the ability of said $\alpha_2$M to undergo conformational changes, and subsequently reacting said limited $\alpha_2$M with a $C_{1-6}$ alkyl-bearing primary amine, in an amount effective to neutralize at least one of TNF-$\alpha$ and IL-1$\beta$ in said mammal.

6. A method of treating mammals in established septic shock, comprising administering thereto a therapeutically effective amount of a compound prepared by reacting $\alpha_2$M with a bi-functional peptide cross-linking agent to limit the ability of said $\alpha_2$M to undergo conformational changes, and subsequently reacting said limited $\alpha_2$M with a $C_{1-6}$ alkyl-bearing primary amine.

7. A pharmaceutical preparation, comprising a compound prepared by reacting $\alpha_2$M with a bi-functional peptide cross-linking agent to limit the ability of said $\alpha_2$M to undergo conformational changes, and subsequently reacting said limited $\alpha_2$M with a $C_{1-6}$ alkyl-bearing primary amine, the resulting conformational intermediate having a high binding affinity for TNF-$\alpha$ and interlukin-1$\beta$.

* * * * *